US012709735B2

(12) United States Patent
Gurtner et al.

(10) Patent No.: US 12,709,735 B2
(45) **Date of Patent: *Aug. 18, 2026**

(54) EFFICIENT STEM CELL DELIVERY INTO BIOMATERIALS USING CAPILLARY DRIVEN ENCAPSULATION

(71) Applicant: The Board of Trustees of The Leland Stanford Junior University, Stanford, CA (US)

(72) Inventors: Geoffrey C. Gurtner, Portola Valley, CA (US); Jayakumar Rajadas, Cupertino, CA (US); Robert C. Rennert, Palo Alto, CA (US); Dominik Duscher, Linz (AT)

(73) Assignee: The Board of Trustees of The Leland Stanford Junior University, Stanford, CA (US)

( * ) Notice: Subject to any disclaimer, the term of this patent is extended or adjusted under 35 U.S.C. 154(b) by 982 days.

This patent is subject to a terminal disclaimer.

(21) Appl. No.: 17/513,200

(22) Filed: Oct. 28, 2021

(65) Prior Publication Data

US 2022/0049214 A1 Feb. 17, 2022

Related U.S. Application Data

(63) Continuation of application No. 14/973,283, filed on Dec. 17, 2015, now Pat. No. 11,174,460, which is a (Continued)

(51) Int. Cl.

| | |
|---|---|
| ***A61K 35/12*** | (2015.01) |
| ***A61P 17/02*** | (2006.01) |
| ***C12N 5/00*** | (2006.01) |

(52) U.S. Cl.

CPC ............ *C12N 5/0068* (2013.01); *A61K 35/12* (2013.01); *A61P 17/02* (2018.01);

(Continued)

(58) Field of Classification Search

CPC combination set(s) only.

See application file for complete search history.

(56) References Cited

U.S. PATENT DOCUMENTS

| | | | |
|---|---|---|---|
| 11,174,460 | B2 | 11/2021 | Gurtner et al. |
| 2011/0305745 | A1 | 12/2011 | Gurtner et al. |

OTHER PUBLICATIONS

Altman AM, Yan Y, Matthias N, Bai X, Rios C, Mathur AB, Song YH, Alt EU. IFATS collection: Human adipose-derived stem cells seeded on a silk fibroin-chitosan scaffold enhance wound repair in a murine soft tissue injury model. Stem Cells. 2009;27(1):250-258.

(Continued)

*Primary Examiner* — Manjunath N Rao
*Assistant Examiner* — Qing Xu
(74) *Attorney, Agent, or Firm* — Levine Bagade Han LLP

(57) ABSTRACT

Efficient stem cell delivery into biomaterials using capillary driven encapsulation are disclosed herein where stem/progenitor and/or tissue specific cells are rapidly and efficiently seeded via capillary driven encapsulation into a porous scaffold for cell delivery in the skin or any other organ. The rapid capillary force approach maximizes both seeding time and efficiency by combining hydrophobic, entropic and capillary forces to promote active, 'bottom-up' cell engraftment. This methodology uses micro domain patterned biopolymers in a porous dry gel to generate capillary pressure to move a viscous stem cell mix from a hydrophobic reservoir into the polymer matrix to promote active cell seeding within the entire gel volume.

14 Claims, 10 Drawing Sheets

Related U.S. Application Data continuation of application No. 14/711,588, filed on May 13, 2015, now abandoned.

(60) Provisional application No. 61/994,340, filed on May 16, 2014.

(52) U.S. Cl.
CPC ...... *C12N 2527/00* (2013.01); *C12N 2533/30* (2013.01); *C12N 2533/54* (2013.01); *C12N 2533/70* (2013.01); *C12N 2535/10* (2013.01)

(56) References Cited

OTHER PUBLICATIONS

Alves et al., Journal of Biomedical material Research, Part A, 2008, 91A:480-488. (Year: 2008).
Amos PJ, Kapur SK, Stapor PC, Shang H, Bekiranov S, Khurgel M, Rodeheaver GT, Peirce SM, Katz AJ. Human adipose-derived stromal cells accelerate diabetic wound healing: impact of cell formulation and delivery. Tissue Eng Part A. 2010;16(5):1595-1606.
Cowan CM, Shi YY, Aalami OO, Chou YF, Mari C, Thomas R, Quarto N, Contag CH, Wu B, Longaker MT. Adipose-derived adult stromal cells heal critical-size mouse calvarial defects. Nat Biotechnol. 2004;22(5):560-567.
De Ugarte DA, Morizono K, Elbarbary A, Alfonso Z, Zuk PA, Zhu M, Dragoo JL, Ashjian P, Thomas B, Benhaim P, Chen I, Fraser J, Hedrick MH. Comparison of multi-lineage cells from human adipose tissue and bone marrow. Cells Tissues Organs. 2003;174(3):101-109.
Gerecht S, Burdick JA, Ferreira LS, Townsend SA, Langer R, Vunjak-Novakovic G. Hyaluronic acid hydrogel for controlled self-renewal and differentiation of human embryonic stem cells. Proc Natl Acad Sci U S A. 2007;104(27):11298-11303.
Greco SJ, Liu K, Rameshwar P. Functional similarities among genes regulated by OCT4 in human mesenchymal and embryonic stem cells. Stem Cells. 2007;25(12):3143-3154.
Hocking AM, Gibran NS. Mesenchymal stem cells: paracrine signaling and differentiation during cutaneous wound repair. Exp Cell Res. 2010;316(14):2213-2219.
Huang SP, Hsu CC, Chang SC, Wang CH, Deng SC, Dai NT, Chen TM, Chan JY, Chen SG, Huang SM. Adipose-derived stem cells seeded on acellular dermal matrix grafts enhance wound healing in a murine model of a full-thickness defect. Ann Plast Surg. 2012;69(6):656-662.
Huang SP, Huang CH, Shyu JF, Lee HS, Chen SG, Chan JY, Huang SM. Promotion of wound healing using adipose-derived stem cells in radiation ulcer of a rat model. J Biomed Sci. 2013;20(1):51.
Lam MT, Nauta A, Meyer NP, Wu JC, Longaker MT. Effective delivery of stem cells using an extracellular matrix patch results in increased cell survival and proliferation and reduced scarring in skin wound healing. Tissue Eng Part A. 2013;19(5-6):738-747.
Leathers TD. Biotechnological production and applications of pullulan. Appl Microbiol Biotechnol. 2003;62(5-6):468-473.
Lee et al., Progress in Polymer Science, 37: 106-126, 2012.
Levi B, James AW, Nelson ER, Vistnes D, Wu B, Lee M, Gupta A, Longaker MT. Human adipose derived stromal cells heal critical size mouse calvarial defects. PLoS One. 2010;5(6):e11177.
Liu S, Zhang H, Zhang X, Lu W, Huang X, Xie H, Zhou J, Wang W, Zhang Y, Liu Y, Deng Z, Jin Y. Synergistic angiogenesis promoting effects of extracellular matrix scaffolds and adipose-derived stem cells during wound repair. Tissue Eng Part A. 2011;17(5-6):725-739.
Lutolf MP, Hubbell JA. Synthetic biomaterials as instructive extracellular microenvironments for morphogenesis in tissue engineering. Nat Biotechnol. 2005;23(1):47-55.
Nakanishi C, Nagaya N, Ohnishi S, Yamahara K, Takabatake S, Konno T, Hayashi K, Kawashiri MA, Tsubokawa T, Yamagishi M. Gene and protein expression analysis of mesenchymal stem cells derived from rat adipose tissue and bone marrow. Circ J. 2011;75(9):2260-2268.
Nie C, Yang D, Xu J, Si Z, Jin X, Zhang J. Locally administered adipose-derived stem cells accelerate wound healing through differentiation and vasculogenesis. Cell Transplant. 2011;20(2):205-216.
Olivares AL, Lacroix D. Simulation of cell seeding within a three-dimensional porous scaffold: a fluid-particle analysis. Tissue Eng Part C Methods. 2012;18(8):624-631.
Pan GJ, Chang ZY, Scholer HR, Pei D. Stem cell pluripotency and transcription factor Oct4. Cell Res. 2002;12(5-6):321-329.
Petrenko YA, Ivanov RV, Lozinsky VI, Petrenko AY. Comparison of the methods for seeding human bone marrow mesenchymal stem cells to macroporous alginate cryogel carriers. Bull Exp Biol Med. 2011;150(4):543-546.
Pittenger MF, Mackay AM, Beck SC, Jaiswal RK, Douglas R, Mosca JD, Moorman MA, Simonetti DW, Craig S, Marshak DR. Multilineage potential of adult human mesenchymal stem cells. Science. 1999;284(5411):143-147.
Prang et al., Biomaterials, 27: 3560-3569, 2006.
Rehman J, Traktuev D, Li J, Merfeld-Clauss S, Temm-Grove CJ, Bovenkerk JE, Pell CL, Johnstone BH, Considine RV, March KL. Secretion of angiogenic and antiapoptotic factors by human adipose stromal cells. Circulation. 2004;109(10):1292-1298.
Rennert RC, Rodrigues M, Wong VW, Duscher D, Hu M, Maan Z, Sorkin M, Gurtner GC, Longaker MT. Biological therapies for the treatment of cutaneous wounds: phase III and launched therapies. Expert Opin Biol Ther. 2013;13(11):1523-1541.
Riekstina U, Cakstina I, Parfejevs V, Hoogduijn M, Jankovskis G, Muiznieks I, Muceniece R, Ancans J. Embryonic stem cell marker expression pattern in human mesenchymal stem cells derived from bone marrow, adipose tissue, heart and dermis. Stem Cell Rev. 2009;5(4):378-386.
Rustad KC, Wong VW, Sorkin M, Glotzbach JP, Major MR, Rajadas J, Longaker MT, Gurtner GC. Enhancement of mesenchymal stem cell angiogenic capacity and stemness by a biomimetic hydrogel scaffold. Biomaterials. 2012;33(1):80-90.
San Juan A, Hlawaty H, Chaubet F, Letourneur D, Feldman LJ. Cationized pullulan 3D matrices as new materials for gene transfer. J Biomed Mater Res A. 2007;82(2):354-362.
Sasaki et al., Journal of Neuroscience, 29: 14932-14941, 2009.
Sen CK, Gordillo GM, Roy S, Kirsner R, Lambert L, Hunt TK, Gottrup F, Gurtner GC, Longaker MT. Human skin wounds: a major and snowballing threat to public health and the economy. Wound Repair Regen. 2009;17(6):763-771.
Service RF. Tissue engineers build new bone. *Science*. 2000;289(5484):1498-1500.
Sung HJ, Hong SC, Yoo JH, Oh JH, Shin HJ, Choi IY, Ahn KH, Kim SH, Park Y, Kim BS. Stemness evaluation of mesenchymal stem cells from placentas according to developmental stage: comparison to those from adult bone marrow. J Korean Med Sci. 2010;25(10):1418-1426.
Suzuki et al., J. Mater Sc. Mater Med., 19: 1307-1315, 2008.
Taha MF, Hedayati V. Isolation, identification and multipotential differentiation of mouse adipose tissue-derived stem cells. Tissue Cell. 2010;42(4):211-216.
Thevenot P, Nair A, Dey J, Yang J, Tang L. Method to analyze three-dimensional cell distribution and infiltration in degradable scaffolds. Tissue Eng Part C Methods. 2008;14(4):319-331.
Wong VW, Rustad KC, Glotzbach JP, Sorkin M, Inayathullah M, Major MR, Longaker MT, Rajadas J, Gurtner GC. Pullulan hydrogels improve mesenchymal stem cell delivery into high-oxidative-stress wounds. Macromol Biosci. 2011;11(11):1458-1466.
Altman AM, Matthias N, Yan Y, Song YH, Bai X, Chiu ES, Slakey DP, Alt EU. Dermal matrix as a carrier for in vivo delivery of human adipose-derived stem cells. *Biomaterials*. 2008;29(10):1431-1442.
Galiano RD, Michaels Jt, Dobryansky M, Levine JP, Gurtner GC. Quantitative and reproducible murine model of excisional wound healing. Wound Repair Regen. 2004;12(4):485-492.
Gurtner GC, Werner S, Barrandon Y, Longaker MT. Wound repair and regeneration. Nature. 2008;453(7193):314-321.

(56) References Cited

OTHER PUBLICATIONS

Kim WS, Park BS, Sung JH, Yang JM, Park SB, Kwak SJ, Park JS. Wound healing effect of adipose-derived stem cells: a critical role of secretory factors on human dermal fibroblasts. J Dermatol Sci. 2007;48(1):15-24.

Rennert RC, Sorkin M, Garg RK, Gurtner GC. Stem cell recruitment after injury: lessons for regenerative medicine. Regen Med. 2012;7(6):833-850.

Shen T, Pan ZG, Zhou X, Hong CY. Accelerated healing of diabetic wound using artificial dermis constructed with adipose stem cells and poly (L-glutamic acid)/chitosan scaffold. Chin Med J (Engl). 2013;126(8):1498-1503.

A
B
Θ = contact angle
γ = surface tension
ρ = liquid density
r = pore radius
g = gravitational force
Porous Hydrogel
Θ
h ≈ 2γcosΘ / ρgr
C
D
Hydrogel Seeding Times by Method
Method
Time
Capillary
1 minute
Centrifuge
10 minutes
Injection
1 minute
Orbital
60 minutes
Seeding Efficiency (%)
100
80
60
40
20
0
Capillary
Centrifuge
Injection
Orbital
*
E
F
Relative Cell Survival Illustration of superhydrophobic driven capillary seeding. Methylene blue colored water is poured on hydrophobic high density liquid (perfluorodecalin, d= 1.92 g/cm$^3$). Liquid droplet is sponged using 5% collagen pullulan hydrogel bioscaffold.

EFFICIENT STEM CELL DELIVERY INTO BIOMATERIALS USING CAPILLARY DRIVEN ENCAPSULATION

CROSS-REFERENCE TO RELATED APPLICATIONS

This application is a continuation of Ser. No. 14/973,283 filed Dec. 17, 2015, which is a continuation of U.S. application Ser. No. 14/711,588 filed May 13, 2015 (now abandoned), which claims the benefit of priority to U.S. Provisional Application No. 61/994,340 filed May 16, 2014, each of which is incorporated herein by reference in its entirety.

STATEMENT OF GOVERNMENT SPONSORED SUPPORT

This invention was made with Government support under contract W81XWH-08-2-0032 awarded by Armed Forces Institute of Regenerative Medicine. The Government has certain rights in this invention.

FIELD OF THE INVENTION

This invention relates to wound healing and tissue regeneration methods.

BACKGROUND OF THE INVENTION

Introduction

Normal wound healing is a complex process involving the coordination of multiple cell and cytokine signaling pathways. These mechanisms can be overwhelmed in the setting of complex injuries and/or underlying disease states, such as diabetes and vascular insufficiency, and ultimately result in the formation of a chronic, non-healing wound. Chronic wounds affect up to 6.5 million U.S. patients and cost in excess of US $25 billion annually. While a variety of treatment modalities are available, stem cell based therapies hold particular promise in this setting due to their strong cytokine profile and potential for multi-lineage differentiation. To optimize this therapeutic approach, biocompatible delivery systems are needed to promote cell survival and cytokine release within the harsh wound environment, with the ideal scaffold recapitulating architectural features of human skin to restore the cell-matrix interactions critical for tissue regeneration.

Our group previously demonstrated that a 5% soft collagen-pullulan hydrogel can be fabricated to closely resemble the three dimensional collagen network of human dermis at a microscopic level and is biocompatible with multiple cell types. Pullulan, a linear homopolysaccharide produced by the fungus *Aureobasidium pullulans*, was specifically chosen for hydrogel construction in conjunction with collagen, as it is biodegradable and nontoxic, making it an attractive biomaterial for tissue engineering approaches. Accordingly, application of unseeded hydrogels in murine excisional wounds was found to increase both the recruitment of stromal cells and formation of vascularized granulation tissue, leading to an improvement in wound closure. Evaluating the capacity of hydrogels for the delivery of cell-based therapies, we have also demonstrated that bone marrow derived mesenchymal stem cells (BM-MSCs) could be engrafted into the hydrogel by co-culture over 14 days, resulting in an increase in BM-MSC stemness factor transcription and growth factor and cytokine secretion. Additionally, application of BM-MSC-seeded hydrogels to murine excisional wounds was found to augment both wound closure rates and angiogenesis when compared to wounds that were untreated or injected with BM-MSCs.

Although BM-MSC delivery to wounds using a hydrogel offers a promising therapeutic opportunity, a source of mesenchymal stem cells other than the bone marrow would be more practical for widespread clinical use. Adipose derived mesenchymal stem cells (ASCs) have several potential advantages over BM-MSCs, including their ease of harvest from human lipoaspirates, as well as their ability to proliferate rapidly and secrete high levels of pro-angiogenic cytokines. Furthermore, the number of BM-MSCs available for isolation from bone marrow drops significantly as people age, potentially requiring larger volumes of bone marrow harvest, which carries greater risk than superficial fat harvest.

Promising preliminary data on the use of human ASCs in vivo has demonstrated their ability to heal critical size calvarial defects, as well as augment vascularization of composite ischemic tissues. Prior work has also shown encouraging results using ASCs embedded in various matrices to improve excisional wound closure, although the clinical translatability of these studies is limited by the prolonged matrix seeding protocols (up to seven days) needed to produce these constructs. In the present study, we describe a capillary seeding method to rapidly engraft ASCs into a lyophilized 5% collagen-pullulan hydrogel at the point of care. Using this efficient hydrogel seeding technique and a splinted murine excisional wound model, we further demonstrate that both murine and human ASC-seeded hydrogels augment wound closure and angiogenesis, and are well suited for clinical adaptation.

SUMMARY OF THE INVENTION

Effective skin regeneration therapies require a successful interface between progenitor cells and biocompatible delivery systems. We previously demonstrated the efficiency of a biomimetic pullulan-collagen hydrogel scaffold for improving bone marrow-derived mesenchymal stem cell survival within ischemic skin wounds by creating a 'stem cell niche' that enhances regenerative cytokine secretion. Adipose-derived mesenchymal stem cells (ASCs) represent an even more appealing source of stem cells due to their abundance and accessibility, and in this study we explored the utility of ASCs for hydrogel-based therapies. To optimize hydrogel cell seeding, a rapid, capillary force-based approach was developed and compared to previously established cell seeding methods. ASC viability and functionality following capillary hydrogel seeding were then analyzed in vitro and in vivo. In these experiments, ASCs were seeded more efficiently by capillary force than by traditional methods, and remained viable and functional in this niche for up to 14 days. Additionally, hydrogel seeding of ASCs resulted in the enhanced expression of multiple stemness and angiogenesis related genes, including Oct4, Vegf, Mcp-1 and Sdf-1. Moving in vivo, hydrogel delivery improved ASC survival, and application of both murine and human ASC-seeded hydrogels to splinted murine wounds resulted in accelerated wound closure and increased vascularity when compared to control wounds treated with unseeded hydrogels. In conclusion, capillary seeding of ASCs within a pullulan-collagen hydrogel bioscaffold provides a convenient and simple way to deliver therapeutic cells to wound environments. Moreover, ASC-seeded constructs display a significant potential to accelerate wound healing that can be easily translated to a clinical setting.

Efficient stem cell delivery into biomaterials using a novel capillary driven encapsulation technique.

In one embodiment of the invention, we have developed a novel technique to rapidly and efficiently seed stem/progenitor and/or tissue specific cells via capillary driven encapsulation into a porous scaffold for cell delivery in the skin or any other organ. The rapid capillary force approach maximizes both seeding time and efficiency by combining hydrophobic, entropic and capillary forces to promote active, 'bottom-up' cell engraftment. This methodology uses micro domain patterned biopolymers (for example collagen or silk) in a porous dry gel (for example pullulan) to generate capillary pressure to move a viscous stem cell mix (SCM) from a hydrophobic reservoir into the polymer matrix. This technique promotes active cell seeding within the entire gel volume. This seeding process is depicted in FIG. 1.

An additional component of this approach is the concept of 'capillary origami', wherein dynamic liquid surface tension is used to shape solid materials (Geraldi, et al. Applied Physics. 2013). Specifically, when solid films/membranes (even if hydrophobic) are allowed to come in contact with aqueous solutions, they tend to bend due to the capillary forces and encircle the aqueous solution to form "liquid marbles". This phenomenon, termed 'capillary origami', has been established for a variety of materials. In the presence of water triangularly cut sheets will curl up due to surface tension and eventually transform into a closed 3D pyramidal structure. In this invention, we use this effect in part to encapsulate stem cells in the collagen or silk or other polymer micro domains (see FIG. 8).

Based on these principals, a gentle, highly efficient encapsulating technology could be envisioned for cell seeding within the bioscaffold by utilizing a mosaic distribution of a polymer matrix (such as collagen domains) or other material within a hydrogel. To further facilitate cell delivery into the matrix, the cell population could be maintained and/or suspended in an aqueous nutrient medium on top of a solid or liquid superhydrophobic substance (see FIG. 9).

The underlying superhydrophobic substance could be composed of the following materials:

1. Formation of patterned roughness on paraffin wax surfaces
2. Formation of Teflon based super hydrophobic surface
3. Formation of pattern with Inject printers
4. High density Perfluorocarbon liquids.

Modulation of Encapsulation Domains Imprinted within Hydrogels to Promote Cell Engraftment.

Encapsulation domains can be prepared by imprinting collagen arrays (or other polymer matrices) within a dry carbohydrate gel (such as pullulan) (see FIG. 10). Collagen or silk or other biodegradable microfilms in this form would curl up to create a microcapsule when exposed to aqueous solution. Such as porous hydrogel is capable of initiating flow of aqueous solution across its volume via capillary action. Thus when the hydrogel is placed over an aqueous solution containing stem cells, a flow of stem cells could be generated across the gel which would eventually reach collagen patches causing them to curl up and ultimately trapping the stem cells along with the nutrient medium into collagen encapsulated stem cells entities.

Advantages

Prior research on scaffold seeding methodologies has focused on increasing seeding efficacy, as a densely seeded construct is crucial for proper tissue formation. Nonetheless, increasingly complex approaches can promote a high seeding density at the expense of time, with existing protocols often lasting up to several hours or even requiring overnight incubation. The rapid capillary force approach described herein maximizes both seeding time and efficiency by combining hydrophobic, entropic and capillary forces to promote active, 'bottom-up' cell engraftment. When compared with three previously described seeding methodologies 'top-down' seeding on an orbital shaker, seeding through centrifugation, and direct-injection seeding, we observed a consistently high seeding efficacy only for orbital shaker seeding and our capillary protocol, with capillary seeding having the additional advantage of being significantly faster than orbital shaking (on the order of minutes as opposed to hours). In fact, capillary seeding was the only seeding methodology tested that allowed for efficient, rapid cell engraftment, with preservation of cell viability and scaffold micro-architecture, making it highly translatable to the clinical setting.

DETAILED DESCRIPTION OF THE INVENTION

Other embodiments, further teachings and/or examples related to the invention are described.

Materials and Methods

Animals:

All mice were housed in the Stanford University Veterinary Service Center in accordance with NIH and institution-approved animal care guidelines. All procedures were approved by the Stanford Administrative Panel on Laboratory Animal Care. All assays were performed in triplicate unless otherwise stated.

Murine Adipose-derived Mesenchymal Stem Cell Isolation:

Wild-type and luciferase+/GFP+ ASCs were isolated from the inguinal fat pads of eight-twelve week old mice (C57BL/6J and FVB-Tg(CAG-luc,-GFP)L2G85Chco/J, respectively; Jackson Laboratories, Bar Harbor, ME), minced and digested for one hour at 37° C. using collagenase I (Roche Applied Science, Indianapolis, IN). The reaction was stopped and the cells were spun down to obtain the stromal vascular fraction (SVF). The SVF was resuspended, strained and plated on plastic culture dishes. Media was changed every 48 hours until cells reached 90% confluence. Cells were used at or before passage two unless otherwise indicated.

Figure 1:
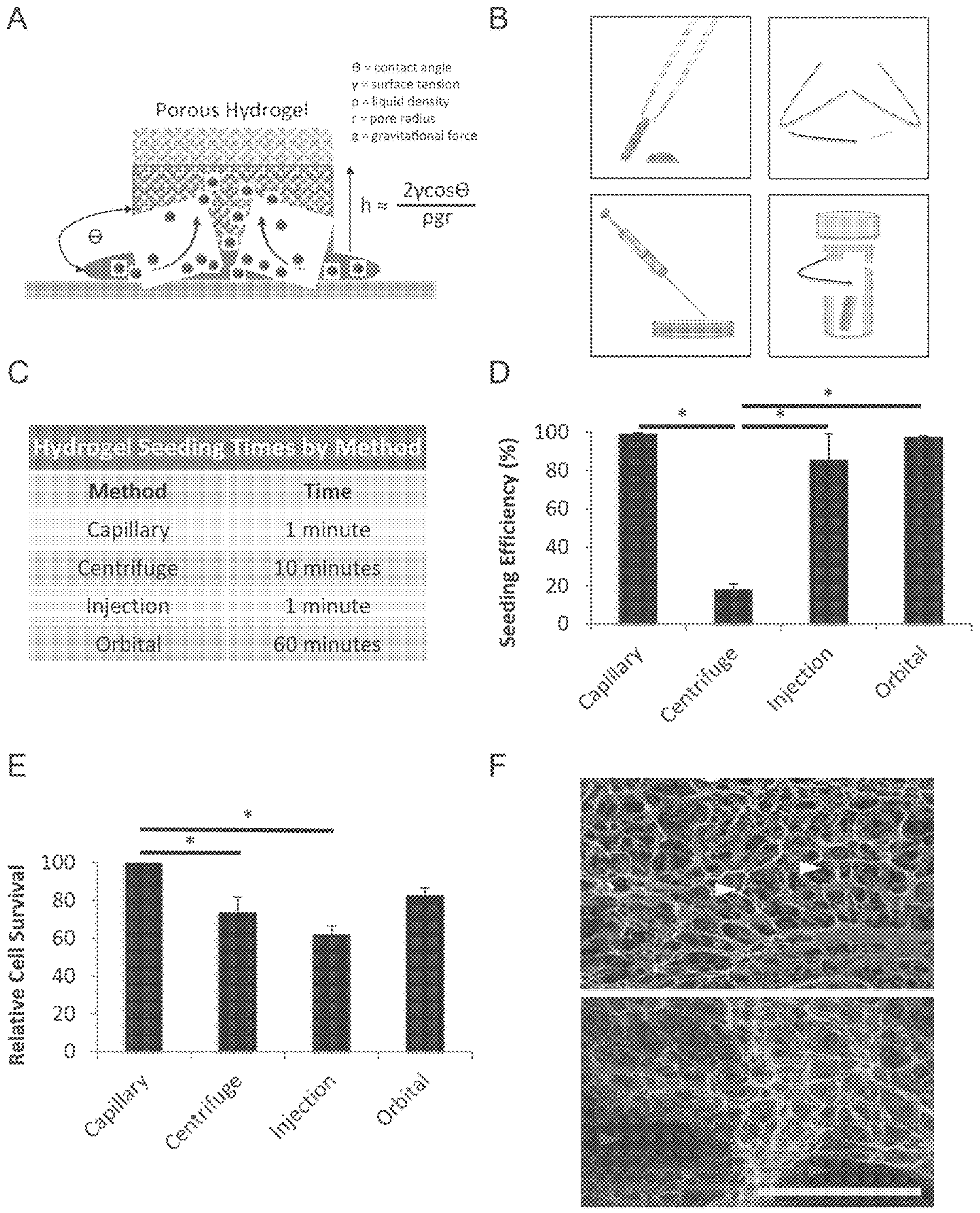
FIG. 1. Efficacy of a Novel Capillary Technique for Scaffold Seeding. (A) A 5% collagen-pullulan hydrogel contains a porous architecture that interfaces with a droplet of suspended ASCs on a hydrophobic surface. Cells are actively engrafted via a combination of hydrophobic, entropic and capillary forces, the last a function of hydrogel pore width and liquid properties of the ASC solution. (B) Capillary seeding was compared to centrifugal, injection and orbital seeding approaches (left upper to right lower corner). (C) Approximate duration of seeding techniques. (D) Quantification of cell seeding efficiency, with capillary and orbital shaker seeding demonstrating a consistently high efficacy. (E) Quantification of seeded cell viability at 72 hours, with capillary seeding resulting in a significantly enhanced survival as compared to centrifuge and injection techniques. (F) Scanning electron micrographs focusing on hydrogel structure demonstrates that while capillary seeding conserves hydrogel micro-architecture (top micrograph, white arrows indicate intact scaffold), injection-seeding damages scaffold architecture (bottom micrograph, gray arrows indicate damaged scaffold). $*p<0.05$. Scale bar=100 μm.

Hydrogel Fabrication and Cell Seeding Optimization:

5% collagen-pullulan hydrogel was produced as described previously. Capillary force seeding was assessed against adaptations of three previously described scaffold seeding approaches (injection, centrifugal and orbital culture), with each technique described in detail below (FIG. 1A-B). For this and all subsequent hydrogel based analyses, dehydrated hydrogel was cut into 6 mm circles using a punch biopsy tool, and seeded with $2.5\times10^5$ ASCs (n=4 hydrogels per analysis). Following the respective seeding technique, hydrogels were placed in excess Dulbecco's Modified Eagle Medium (DMEM) solution supplemented with 10% fetal bovine serum (FBS) and 1% penicillin/streptomycin (Life Technologies, Grand Island, NY) and cultured for cell viability and scanning electron microscopy (SEM) structural analyses. Seeding efficiency was also determined by counting residual cells in cell seeding media for each methodology with a hemocytometer. Following this comparative analysis, capillary seeding was used for all subsequent experiments.

To achieve capillary seeding, $2.5\times10^5$ murine ASCs (mASCs) suspended in 15 μl of DMEM solution was pipetted onto hydrophobic wax paper and the hydrogel was immediately placed on top. Cells were absorbed actively into the pores of the scaffold by capillary, hydrophobic and entropic forces, and became visibly saturated within 1 minute (completely hydrated with negligible media/cells remaining on wax paper upon lifting of the hydrogel). Centrifugal seeding was achieved by combining $2.5\times10^5$ mASCs (diluted in 200 μl of media) and a hydrogel in a 1.5 mL Eppendorf tube. Following saturation of the hydrogel in excess media, the tube was subjected to three rounds of centrifugation at 3000 rpm for two minutes, interrupted by vortexing for 10 seconds. Injection seeding was completed by injecting $2.5\times10^5$ mASCs suspended in 30 μl of media into the center of each hydrogel using a 25-gauge needle. Orbital seeding was achieved by placing each hydrogel in 100 μl of media on a 48-well plate, followed by application of $2.5\times10^5$ mASCs suspended in 15 μl of media on top of each hydrogel, and rocking on an orbital shaker for 1 hour at 37° C.

SEM Analysis:

High-resolution scanning electron microscopy (SEM) of ASC-seeded hydrogels was completed using a Hitachi 3400N VP scanning electron microscope (Hitachi High Technologies America, Inc., Schaumburg, Illinois) at the Stanford Cell Sciences Imaging Facility.

In Vitro Cell Viability/Migration/Proliferation:

A live-dead assay was performed to assess ASC viability following hydrogel seeding according to manufacturer's instructions (Live/Dead Cell Viability Assay, Life Technologies).

To confirm cell migration through the hydrogel, a modified transwell assay was performed. Briefly, ASCs were seeded by capillary force onto 6 mm hydrogels and placed in the top chamber of an 8.0 μm HTS Transwell-96 Well Plate (Corning Life Sciences, Tewksbury, MA) with mouse PDGF-BB as the chemoattractant. Twenty-four hours later, membranes were removed and fixed with 4% paraformaldehyde. Nuclei were stained with VectaShield Mounting Medium with DAPI and analyzed using fluorescence microscopy.

ASC proliferation was compared between hydrogel-seeded cells and plated cells using an MTT assay (Vybrant MTT Cell Proliferation Assay Kit, Invitrogen, Grand Island, NY).

In Vitro Real-time Quantitative PCR Analysis:

ASCs were capillary-seeded onto scaffolds or plated into each well of a 6-well plate and incubated at 37° C. in 5% $CO_2$ for 24-48 hours. Total RNA was harvested from hydrogel-seeded and plated ASCs as previously described, and converted to cDNA through reverse transcription (Superscript First-Strand Synthesis Kit, Invitrogen). Real-time qPCR reactions were performed using Taq polymerase, magnesium salts, dNTPs, and a reaction buffer formulated as a 2× Universal Taqman® PCR Master Mix (Applied Biosystems, Foster City, CA) and labeled probes and PCR primers formulated as Taqman® gene expression assays for murine Pou5f1 (Oct4, Mm00658129g), Cxcl12 (Stromal cell-derived factor-1/Sdf-1, Mm00445552_m1), Ccl2 (Monocyte chemoattractant protein-1/Mcp-1, Mm00441242_m1), Fgf-2 (Fibroblast growth factor-2, Mm00433287_m1), Igf-1 (Insulin-like growth factor-1, Mm00439560_m1), Vegf-a (Vascular endothelial growth factor-A, Mm01281447_m1), Eng (Endoglin, Mm00468256_m1), Hgf (Hepatocyte growth factor, Mm01135193_m1) andAngpt1 (Angiopoietin 1, Mm00456503_m1) using a Prism 7900HT Sequence Detection System (Applied Biosystems, Carlsbad, CA). Levels of murine Actb (Beta actin, Mm01205647_g1) were quantified in parallel as an internal control and gene expression was normalized.

In Vitro Stemness Factor/Angiogenic Cytokine Quantification and Western Blot:

Total protein was collected from murine ASCs capillary-seeded onto hydrogels or plated for 24-48 hours with RIPA buffer (Sigma-Aldrich, St Louis, MO) in combination with a protease inhibitor. Angiogenic cytokine protein levels were quantified using a Mouse Angiogenesis Array Kit (R&D Systems, Minneapolis, MN). Pixel density of each spot in the array was quantified and normalized to controls using ImageJ (NIH, Bethesda, MD).

For western blot analysis, protein was separated on a 4-12% polyacrylamide gel (Invitrogen), and then transferred to a nitrocellulose membrane (Invitrogen). Anti-Oct4 (1:800, Abcam, Inc, Cambridge, MA) and anti-R-actin were used as the primary antibodies. An HRP-conjugated secondary antibody was used (1:10,000) and detected using the ECL Plus Western Blotting Detection Kit (GE Healthcare, Waukesha, WI).

In vitro Flow Cytometric Analysis of Cell Stemness:

Plated and hydrogel-seeded murine ASCs were analyzed via flow cytometry for expression of alkaline phosphatase using a monoclonal anti-alkaline phosphatase (ALP) antibody (Abeam; 2° FITC-conjugated anti-Rb antibody, Life Technologies) following cell fixation and permeabilization. Mesenchymal stem cell markers were assessed via flow cytometry using the following anti-murine monoclonal antibodies: CD90-PeCy7 (eBioscience, San Diego, CA) and CD44-APC (BD Biosciences, San Jose, CA). All analyses were performed on an LSRII Flow Cytometer (BD Biosciences).

In Vitro Immunofluorescence:

$2.5\times10^5$ murine ASCs seeded onto coverslips or onto hydrogel scaffolds for 24 hours were fixed in 4% paraformaldehyde for 1 hour then incubated with a primary antibody against Oct4 (1:200, Abcam), followed by AlexaFluor 594-conjugated secondary antibody (Invitrogen). Cell nuclei were stained with DAPI.

In Vivo Excisional Wound Model:

Eight-twelve week old male C57Bl/6 mice (Jackson Labs) were randomized to two treatment groups: unseeded hydrogel control or murine ASC-seeded hydrogel. As previously described, two 6 mm full thickness wounds per mouse were excised from either side of the midline. Each wound was held open by donut shaped silicone rings fastened with 6-0 nylon sutures to prevent wound contraction. For mice in the unseeded hydrogel control group, a 6 mm piece of hydrogel saturated with PBS was placed in each wound bed. For mice in the ASC-seeded hydrogel group, a 6 mm piece of hydrogel-seeded by capillary force with ASCs was placed in the wound bed. All wounds were covered with an occlusive dressing (Tegaderm, 3M, St. Paul, MN). Digital photographs were taken on day 0, 1, 3, 5, 7, 9, 11, 14. Wound area was measured using ImageJ software (NIH) (n=6 wounds/group). This model was repeated in its entirety with human ASCs and eight-twelve week old nude male B6.Cg-Foxn1nu/J mice (Jackson Labs).

In Vivo Bioluminescence Imaging:

Viability of ASCs was assessed in vivo in wild-type mice using bioluminescence imaging (n=6 wounds/condition). Wounded mice treated with $2.5\times10^5$ luciferase+ ASCs either seeded on hydrogels or injected circumferentially in the wound bed (4 injection sites at 12, 3, 6 and 9 o'clock as previously described) were anesthetized and injected with 150 mg/kg luciferin in PBS intraperitoneally. Images were obtained 10 minutes later with a cooled CCD camera using the Xenogen IVIS 200 System (Caliper Life Sciences, Mountain View, CA). Luminescence was quantified as units of total flux in an area of interest subtracted from the background luminescence. Images were taken on day 0, 3 and every other day thereafter until day 14.

In Vivo ASC Localization:

Hydrogel-only and murine GFP+ ASC-seeded hydrogel treated wounds were harvested on day 10 from wild-type mice (FVB/NJ, Jackson Laboratories) and immediately embedded in OCT (Sakura Finetek USA, Inc., Torrance CA) for histologic localization of GFP+ cells and CD31 immunohistochemical stain as described below.

Human ASC Isolation:

Human lipoaspirates were collected from healthy, adult female patients with approval from the Stanford Institutional Review Board, and digested in a similar fashion as described for murine adipose tissue. The freshly obtained human SVF was purified via fluorescence-activated cell sorting (FACS) to obtain ASCs (defined as the CD45−/CD31−/CD34+ cell fraction) using the following mouse anti-human monoclonal antibodies: CD31-PE, CD45-PeCy7 and CD34-APC (BD Biosciences). This surface marker profile was chosen to exclude hematopoietic and endothelial cells, and was used in combination with propidium iodide to eliminate dead cells. FACS was performed on a BD FACSAria (BD Biosciences, San Jose, CA), with sorted cells collected for immediate use ($2.5\times10^5$ cells/wound) without culture expansion.

Assessment of Wound Vascularity:

Wound vascularity was assessed utilizing hematoxylin and eosin (H&E) histological examination and/or immunohistochemical staining for the endothelial cell marker CD31 (n=6 wounds/condition). Briefly, wounds from the excisional model were harvested upon closure and either processed for paraffin sectioning or immediately embedded in OCT (Sakura Finetek USA, Inc., Torrance CA). H&E immunohistochemical staining of seven micron thick paraffin sections was used to assess microvessel density. For dermal microvessel counts, luminal structures containing red blood cells were considered microvessels. For each condition, four high-powered fields at 400× were examined for three separate wound samples by three independent blinded observers.

Immunohistochemical staining of seven micron thick frozen sections for CD31 was also used to quantify wound vascularity as described previously. Briefly, slides were fixed in pre-cooled acetone for 10 minutes, washed in PBS, and blocked in a humidified chamber for two hours. Primary antibody (1:100 Rb a CD31, Ab28364, Abeam, Cambridge, MA) was incubated overnight at 4° C., followed by secondary antibody staining (1:400 AF547 Gt a Rb, Life Technologies). Cell nuclei were visualized with the nuclear stain DAPI. ImageJ (NIH) was used to binarize immunofluorescent images taken with the same gain, exposure, and excitation settings as previously described. Intensity threshold values were set automatically and quantification of CD31 staining was determined by pixel-positive area per high power field.

Wound Angiogenic Cytokine Quantification:

mASC treated and control wounds were harvested at day 5, snap frozen in liquid nitrogen and stored at −80° C. Total protein was isolated from wounds using RIPA buffer (Sigma-Aldrich) in combination with a protease inhibitor, and levels of VEGF and HGF were quantified using a mouse quantikine ELISA kit (R&D Systems, Minneapolis, MN).

Statistical analysis:

All values are expressed as mean±SEM. Statistical significance across seeding methods was determined using a one-way ANOVA, with subsequent comparisons between individual methods completed using a Tukey post-hoc analysis. Subsequent data analyses were performed using a Student's t-test. P values≤0.05 were considered statistically significant.

Results

Efficiency of Hydrogel Seeding Via Capillary Force

To determine the most effective cell-seeding methodology, a rapid, capillary force technique (FIG. 1A) was assessed against three previously described scaffold seeding approaches (injection, centrifugal and orbital culture) (FIG. 1B), with regards to seeding time and efficiency, cell survival and maintenance of structural integrity of the hydrogel.

In comparison to the other protocols, capillary force seeding possessed the most optimal combination of speed, efficiency, cell survival and maintenance of hydrogel structure (FIG. 1C-F). Specifically, capillary seeding led to ASC engraftment within 1 minute (FIG. 1C), and was found to be significantly more efficient then centrifugal seeding (99.38%±0.38 vs 18.22%±2.7, $p<0.01$) (FIG. 1D). Capillary seeding was also associated with greater cell viability as compared to both centrifugal and injection seeding ($p<0.02$) (FIG. 1E). Finally, SEM evaluation of scaffolds revealed that injection seeding substantially disrupted the hydrogel microarchitecture as compared to capillary and other seeding approaches (FIG. 1F). Given the overall superiority of the capillary seeding approach, this technique was utilized for all subsequent experiments.

Since the size of a collagen domain can be precisely controlled and amount of stem cells in the culture medium can be accurately determined, it is thus possible to estimate and control the number of cells that will be trapped in each collagen marble. This would be extremely helpful in determining the effective therapeutic dose in future experiments.

Example 1

Preparation of Pullulan Hydrogel with 5% Collagen Domain:

1. Pullulan (1 g), sodium trimetaphosphate (STMP) (1 g) and potassium chloride (KCl) (1 g) were mixed thoroughly in 4.5 mL of MilliQ water. The mixture was vortexed repeatedly until a clear solution was obtained. To the mixture maintained on ice 0.625 mL of 1N sodium hydroxide (NaOH) was added. The above viscous solution was immediately transferred and spread evenly on a 100 sq. cm flat teflon-sheet tray. The gel was allowed to crosslink and dry overnight at room temperature in a sterile environment.
2. The dried hydrogel was washed with sterile water to remove the excess NaOH. The washing step was repeated until the pH of the wash reaches neutral and remains constant
3. 50 mg of collagen type-1 (5 mL of 10 mg/mL (Collagen I, high concentration rat tail 100 mg) and 150 mg Polyvinyl pyrolidine of (molecular weight 10,000 D) are poured on a patterned PDMS membrane under vacuum. After drying, the film was peeled and embossed with the lyophilized hydrogel prepared as above. This was hydrated and washed.
4. The wet hybrid hydrogel was frozen and lyophilized to obtain a dry spongy hydrogel. The hydrogels were stored under sterile conditions until used for experiments.

Example 2

To achieve capillary seeding with the method of this invention, cells are suspended as a single cell solution in saline and pipetted onto hydrophobic patterned wax paper (or superhydrophobic material). A biomaterial (5% collagen in pullulan) is immediately placed on top. Cells are absorbed actively into the pores of the scaffold by capillary, hydrophobic and entropic forces, which becomes visibly saturated within 1 minute (completely hydrated with negligible media/cells remaining on wax paper upon lifting of the hydrogel). The concept of 'capillary origami' also plays a role in this approach, wherein dynamic liquid surface tension is used to shape solid materials. In the setting of capillary cell seeding of bioscaffolds, this surface tension theoretically deforms the scaffold microstructure around the absorbed cell/liquid mix, promoting long-term cell retention within the scaffold (see FIG. 8).

Embodiments of the invention can be varied. For example depending on the application, stem/progenitor or tissue specific cells from various sources can be seeded with the same approach. The biomaterial can also be varied by changing pore size or composition, with these variables affecting the capillary seeding forces. The hydrophobic seeding surface can be altered to affect cell solution and seeding properties. These surfaces can be solid or liquid, and cells can be pre-seeded on them where the surface can provide ideal nutrient/oxygenation conditions until scaffold seeding and ultimate application.

ASCs are Biocompatible with Biomimetic Pullulan-Collagen Hydrogel Scaffolds

Figure 2:
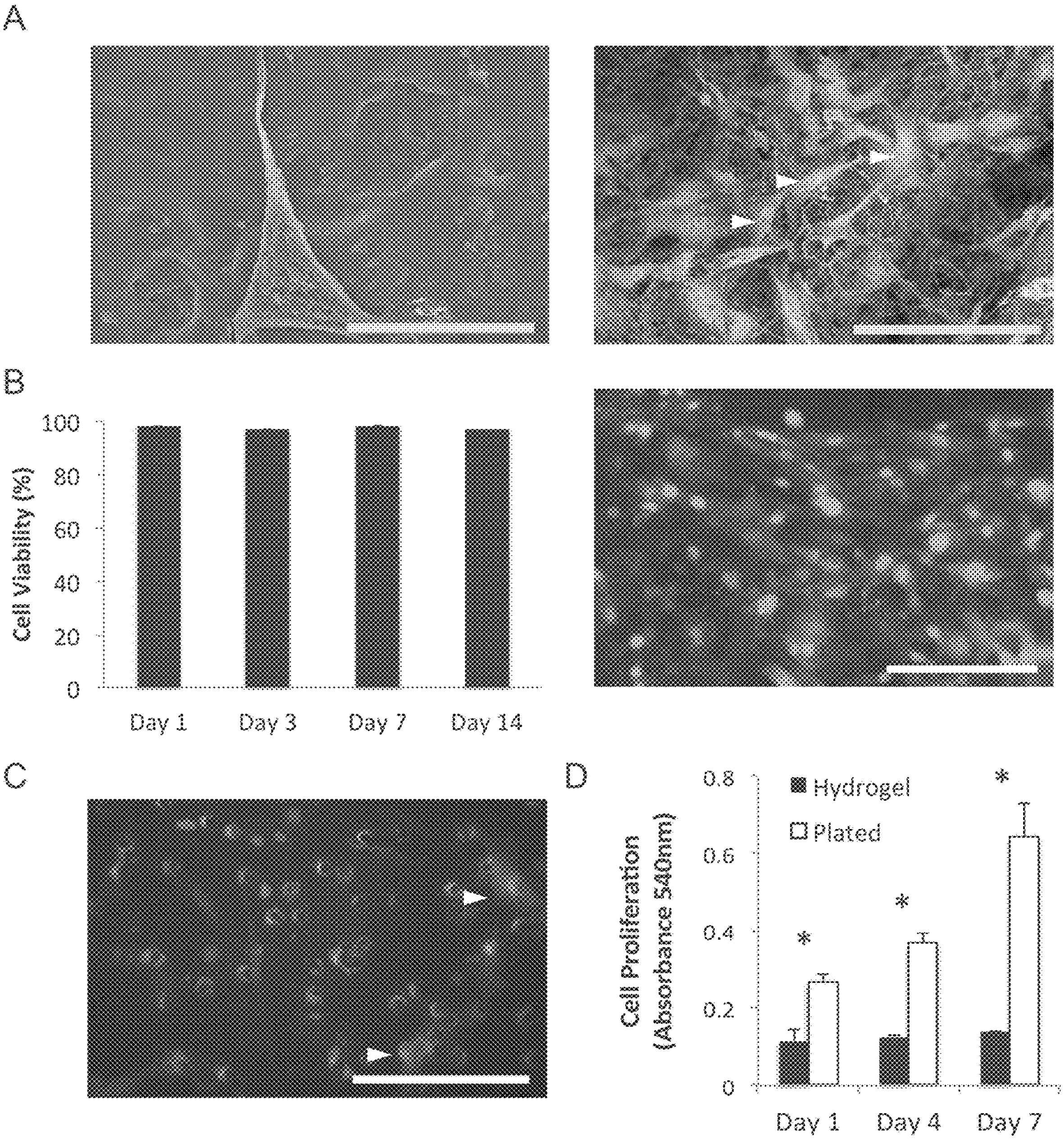
FIG. 2. ASCs are Biocompatible with a Pullulan-Collagen Hydrogel. (A) Electron microscopy images reveal ASCs integrated into the hydrogel scaffold with cytoplasmic extensions into the surrounding three-dimensional matrix (left panel). Cells (white arrowheads) are found interspersed around, between, and within pores (black arrowheads) in a dynamic three-dimensional environment (right panel). Scale bar=30 μm. (B) A live dead assay demonstrates >96% cell viability in the hydrogel through day 14. In the right panel, live cells appear green and dead cells appear red at 14 days. Scale bar=100 μm. (C) A transwell migration assay at 24 hours reveals that ASCs (GFP+ cells indicated by white arrowheads) have migrated onto a permeable membrane below the hydrogel. Scale bar=100 μm. (D) MTT proliferation assay demonstrates a steady increase in metabolic activity among plated ASCs compared to a relatively constant metabolic activity among hydrogel-seeded ASCs. $*p<0.05$. Data are means±one SEM.

Engrafted ASCs were further investigated for biocompatibility within the hydrogel. SEM analysis of capillary seeded hydrogels demonstrated that ASCs became suspended in the three dimensional matrix, and formed cytoplasmic extensions projecting in and around scaffold micropores (FIG. 2A). A live-dead assay was next performed to determine longer-term cell viability in vitro, which remained greater than 96% over a 14-day time frame (FIG. 2B). Engrafted cells also retained their ability to migrate through the hydrogel, a crucial function for in vivo application of cells to the wound bed, as demonstrated by a transwell migration assay (FIG. 2C). Finally, ASC proliferation/metabolic activity was determined using an MTT assay. Plated ASCs demonstrated an increase in metabolic activity over a 7-day period, whereas metabolic activity in hydrogel engrafted ASCs did not increase ($p<0.05$) (FIG. 2D). Given the sustained cell viability observed following hydrogel engraftment in vitro, these data suggested that the hydrogel preserved ASCs in a quiescent state and created a functional niche.

Hydrogel Engrafted ASCs Demonstrate Augmented Wound Healing Potential In Vitro

Figure 3:
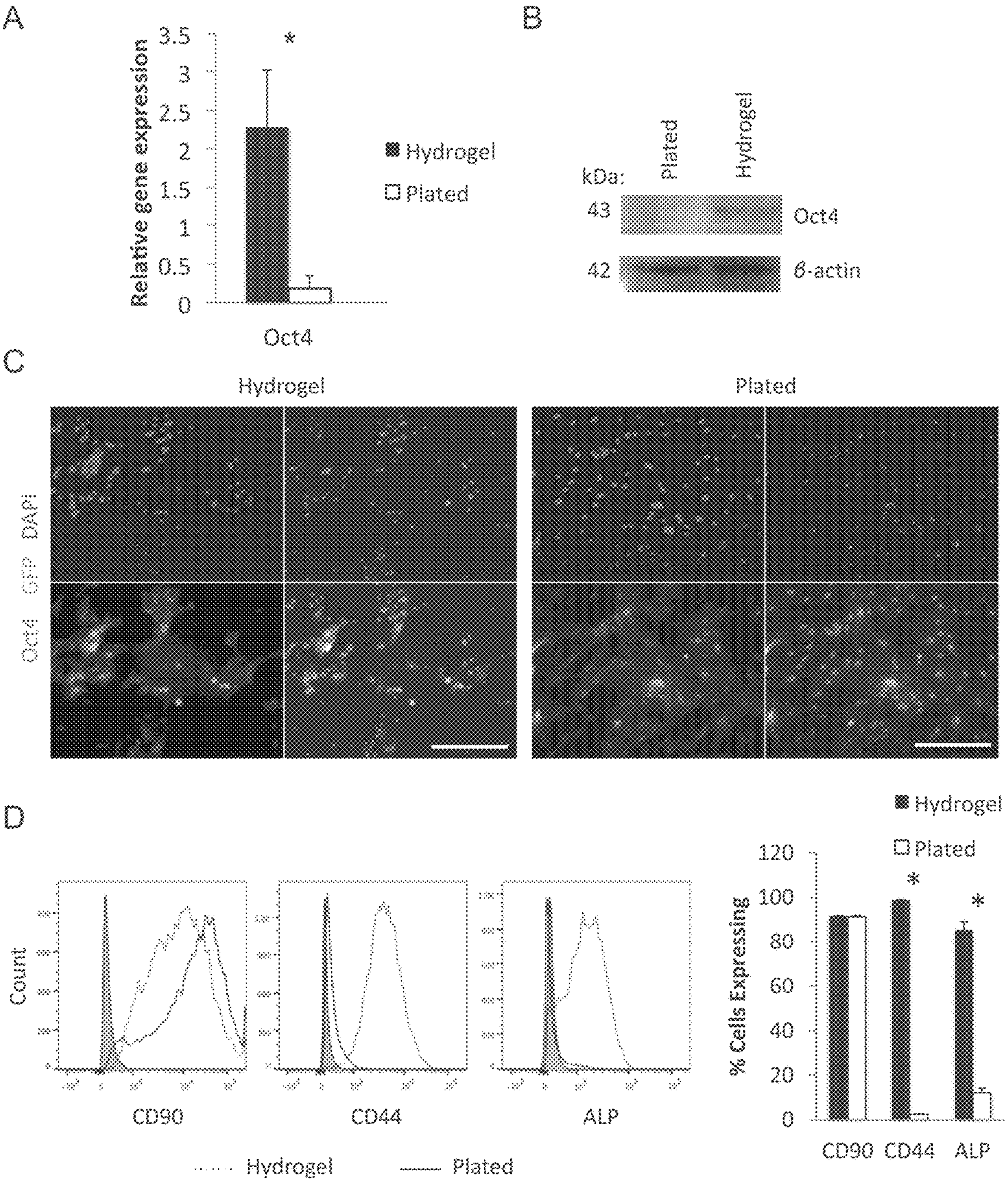
FIG. 3. Hydrogel Engraftment Augments ASC Stemness. (A) qRT reveals an increase in Oct4 transcriptional levels among hydrogel-seeded ASCs compared to plated cells. (B) Immunoblot confirms the increased presence of Oct4 protein expression in hydrogel-seeded ASCs compared to plated ASCs. (C) Immunofluorescence staining similarly demonstrates that ASCs cultured within the hydrogel express increased levels of Oct4 compared to plated cells. (D) Flow cytometric analysis demonstrates increased expression of selected stemness and mesenchymal stem cell markers upon hydrogel seeding (left panel—representative histograms with gray histogram representing the negative control; right panel—quantification). *$p<0.05$. Data are means±one SEM. Scale bar=100 μm.

In order to determine the effects of hydrogel engraftment on ASC wound healing potential, plated murine ASCs and hydrogel-seeded ASCs were compared for their expression of stemness-related proteins, growth factors and cytokines related to wound healing. After 24-48 hours of being plated or seeded in hydrogels, ASC RNA was isolated and qRT-PCR was performed, revealing a significant increase in expression of the sternness related transcription factor Oct4 in hydrogel-seeded versus plated cells (2.28±0.73 vs. 0.18±0.17, $p=0.02$) (FIG. 3A). Western blotting and immunofluorescence staining confirmed an increase in Oct4 expression among hydrogel engrafted ASCs compared to plated cells (FIG. 3B-C).

Flow cytometric analysis for the pluripotency related marker ALP and mesenchymal stem cell markers (CD90 and CD44) further demonstrated an enhancement of ASC stemness following hydrogel seeding (FIG. 3D).

Figure 4:
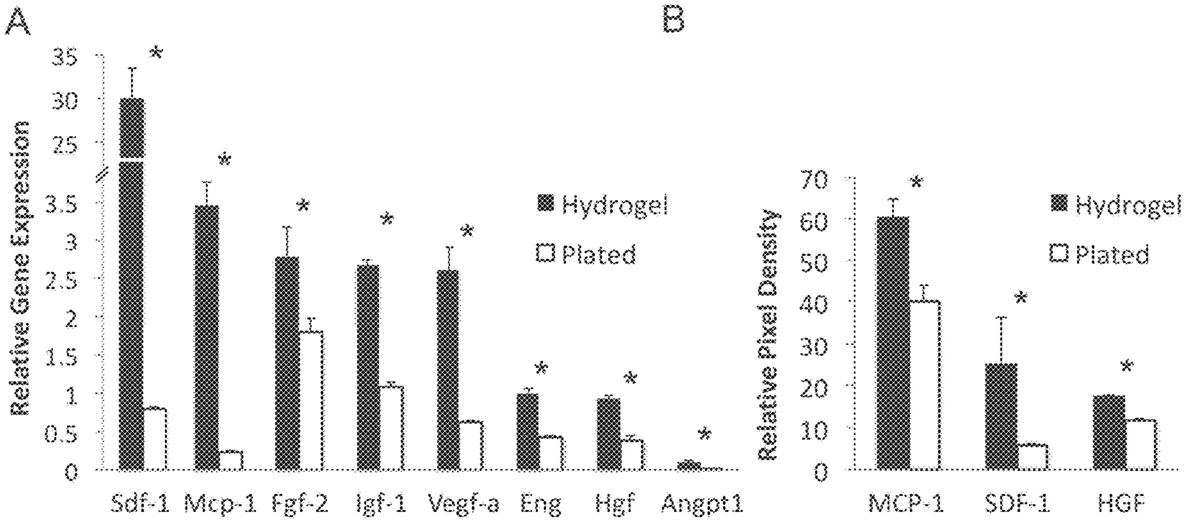
FIG. 4. Hydrogel Engraftment Augments ASC Growth Factor and Cytokine Expression. (A) Multiple growth factors and cytokines demonstrate increased transcriptional levels among hydrogel-seeded ASCs compared to plated cells. (B) Protein confirmation of the upregulation of selected angiogenesis related genes via angiogenic array. *$p<0.05$. Data are means±one SEM.

In addition, hydrogel seeding of ASCs resulted in augmented gene expression of multiple growth factors and cytokines related to angiogenesis and wound healing when compared to standard culture techniques (FIG. 4A). Relative expression of Sdf-1 was significantly increased in hydrogel-seeded ASCs (30.48±4.61 vs. 0.80±0.04, $p=0.0002$), in addition to Mcp-1 (3.44±0.31 vs. 0.23±0.01, $p=6.07\times10^{-6}$), Fgf-2 (2.77±0.38 vs. 1.79±0.17, $p=0.04$), Igf-1 (2.66±0.06 vs. 1.08±0.04, $p=2.94\times10^{-9}$), Vegf-a (2.59±0.31 vs. 0.62±0.01, $p=0.0002$), Eng (1.00±0.06 vs. 0.43±0.01, $p=2.49\times10^{-5}$), Hgf (0.93±0.03 vs. 0.38±0.05, $p=1.03\times10^{-5}$) and Angpt1 (0.10±0.01 vs. $0.003\pm5.79\times10^{-5}$, $p=6.86\times10^{-6}$). To confirm the transcriptional data, protein was isolated and the relative levels of selected angiogenesis related proteins were quantified using a murine angiogenesis array (FIG. 4B). Significantly increased protein levels of MCP-1 (60.54±4.11 vs. 40.23±3.70, $p=0.03$), SDF-1 (25.24±11.15 vs. 5.65±0.74, $p=0.04$) and HGF (17.79±0.04 vs. 11.72±0.56, $p=0.004$) were found in samples isolated from hydrogel-seeded ASCs compared to those plated under standard conditions. The augmentation of ASC stemness and angiogenesis related proteins suggested that the hydrogel scaffold may be an effective cell delivery system for enhancing wound regeneration.

ASC-Seeded Bioscaffolds Result in Sustained Cell Delivery to Excisional Wounds

Figure 5:
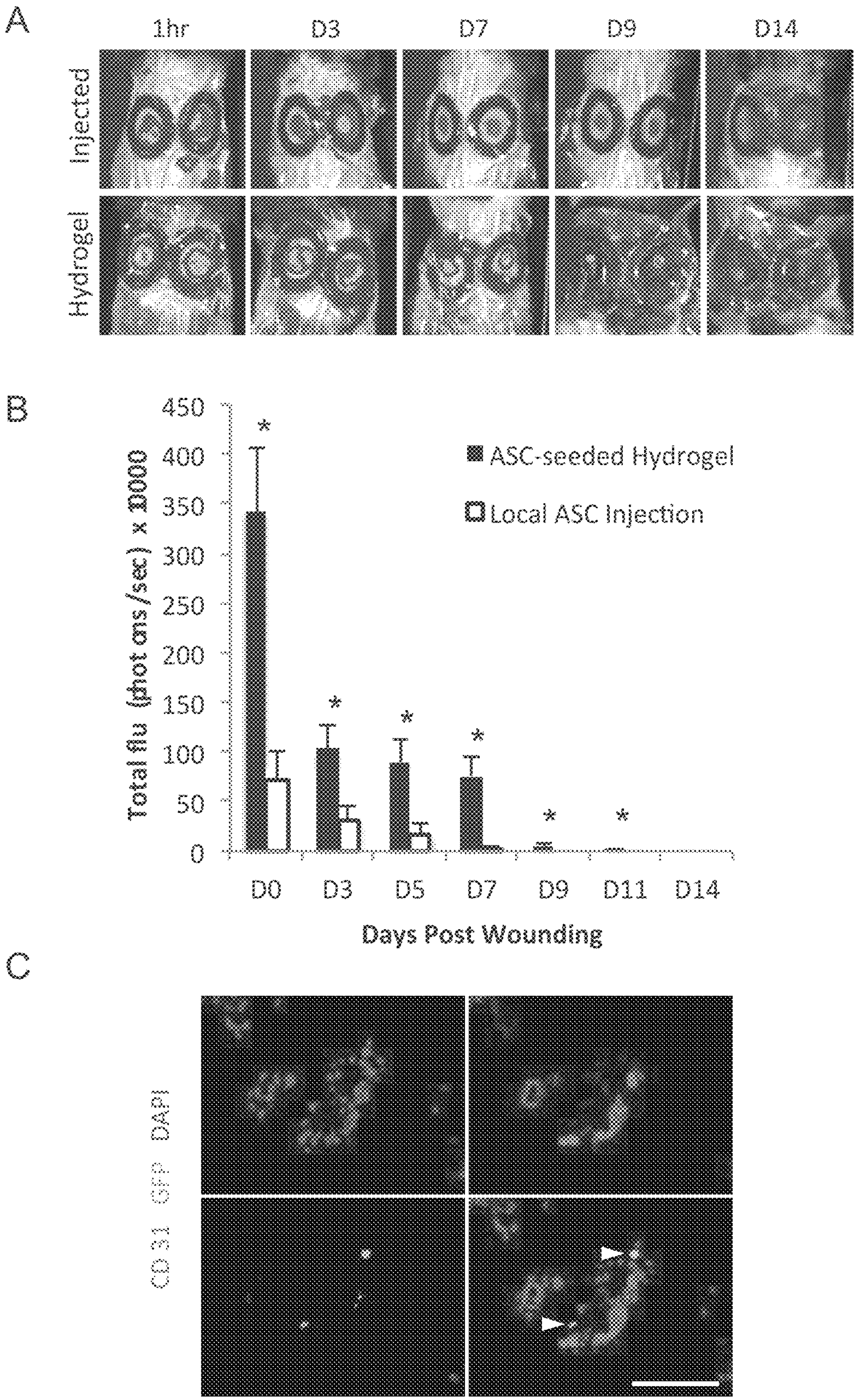
FIG. 5. Hydrogels Promote Sustained ASC Delivery to Murine Wounds. (A) In vivo imaging of luciferase+ ASCs delivered to murine excisional wounds by local injection or topical bioscaffold reveals prolonged cell viability in the hydrogel treatment group. (B) Graphical representation of luciferase signal in ASC-seeded hydrogel treated wounds compared to local ASC injection. ASC-seeded hydrogels result in a significant increase in cell viability and a sustained period of cell delivery relative to injected cells. (C) Co-visualization of GFP+ ASCs with CD31 staining demonstrates the presence of hydrogel-delivered ASCs in the perivascular space (white arrowheads). *$p<0.05$. Data are means±one SEM. Scale bar=100 m.

Given these promising in vitro findings, in vivo experiments were performed to determine whether a pullulan-collagen hydrogel enhanced cell viability. Murine stented excisional wounds were therefore treated with local injection or hydrogel delivery of luciferase expressing ASCs, and bioluminescence imaging revealed a significant improvement in cell viability with hydrogel delivery of ASCs over a 14-day time period (FIG. 5A,B). At 1 hour following ASC treatment, bioluminescence had already decreased dramatically between hydrogel bioscaffold and local injection groups (342.31±63.86 vs. 72.73±29.28, $p=0.003$). By day 9, there was no further evidence of viable cells in injection treated mice, whereas cell viability was sustained in the hydrogel treatment group through day 11 ($p<0.05$).

Having demonstrated that ASCs engraft within the wound, visualization of GFP+ ASCs in conjunction with a cell specific marker was performed on day 10 wounds to investigate ASC localization. Using CD31 as a marker for blood vessel endothelium, GFP+ ASCs delivered into wounds via a hydrogel scaffold were found within the perivascular space (FIG. 5C), consistent with an active role in supporting wound neovascularization.

ASC-Seeded Hydrogels Improve Wound Closure and Vascularization by Increased Pro-Angiogenic Cytokine Expression Having established that delivery of ASCs to wounds is sustained using a pullulan-collagen hydrogel, further experiments were conducted to determine whether wound healing was improved. Wild-type mice were subjected to the stented excisional wound model and wounds were followed for 14 days. Mice that were treated with mASC-seeded hydrogels healed significantly faster than control mice treated with PBS-soaked hydrogels (FIG. 6A), despite similar scaffold resorption kinetics in both groups. Wound area was significantly smaller in the mASC hydrogel treated group compared to control wounds at days 9 and 11 (day 9: 26.88 $mm^2$±2.56 vs 41.79 $mm^2$±4.49, $p=0.04$; day 11: 1.38 $mm^2$±0.9 vs 18.06 $mm^2$±4.85, $p=0.02$), and mASC hydrogel treated wounds closed on average 3 days earlier than controls ($p<0.05$).

Figure 6:
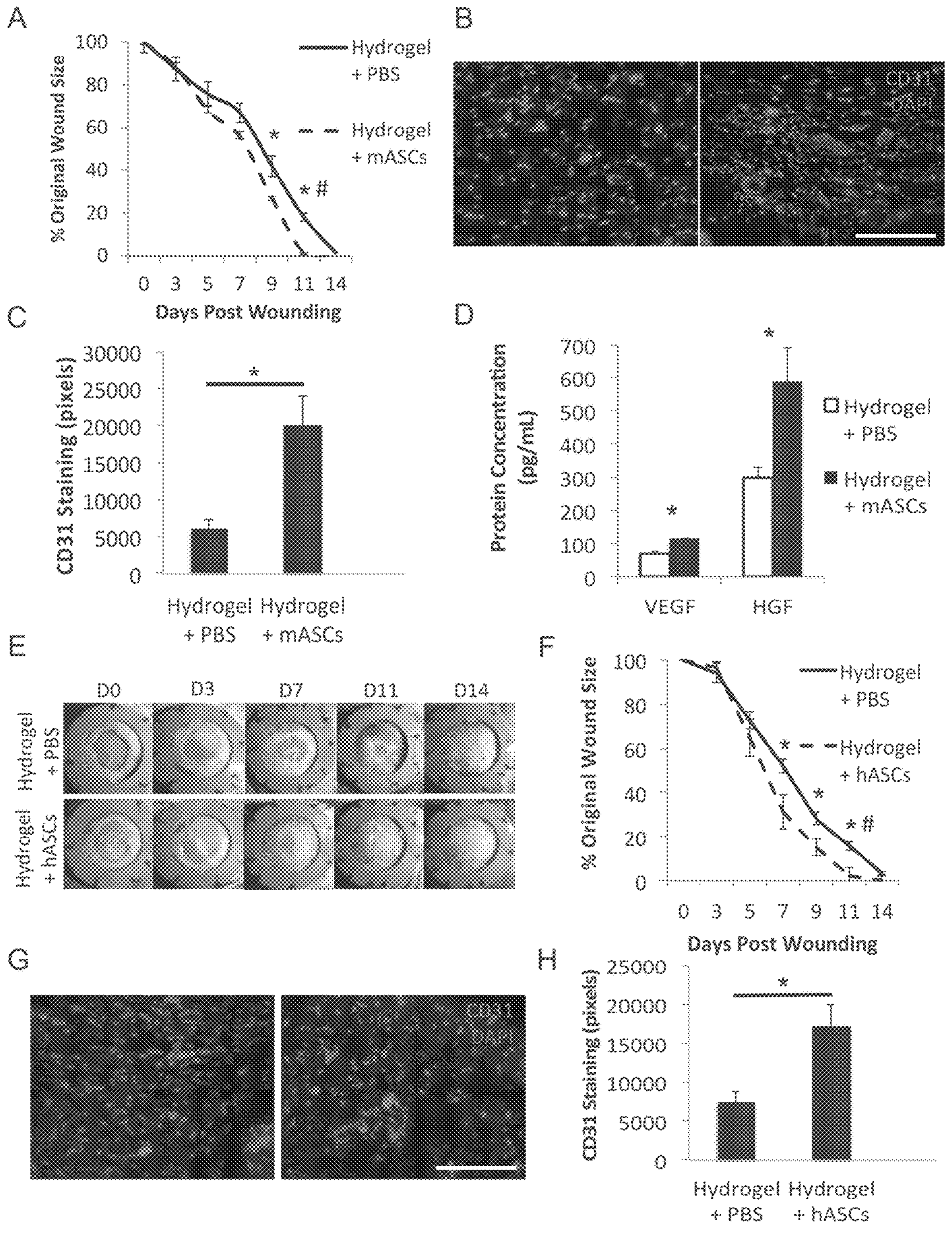
FIG. 6. Murine and Human ASC-Seeded Hydrogels Improve Cutaneous Wound Healing and Vascularization. (A) Wound closure rates were significantly faster among mASC-seeded hydrogels at days 9 and 11, and closed an average of 3 days earlier than controls. (B) CD31 staining confirmed a significant increase in microvessels among the mASC-seeded hydrogel group. DAPI=nuclear stain. Scale bar 100 μm. (C) Quantification of CD31 stained pixels. (D) Evaluation of angiogenic cytokine levels within the wound demonstrates a significantly higher level of VEGF and HGF with ASC treatment. (E) Representative excisional wounds demonstrate a more rapid and earlier time to wound closure among mice treated with hASC-seeded hydrogels compared to controls. (F) Wound closure rates were significantly faster following hASC-seeded hydrogels treatment at days 7, 9, and 11 and closed an average of 2.3 days earlier than controls. (G,H) CD31 staining and pixel quantification confirmed a significant increase in microvessels among the mASC-seeded hydrogel group. *$p<0.05$; # indicates significance in time to closure. All scale bars=100 μm. All data are means±one SEM.
Figure 7:
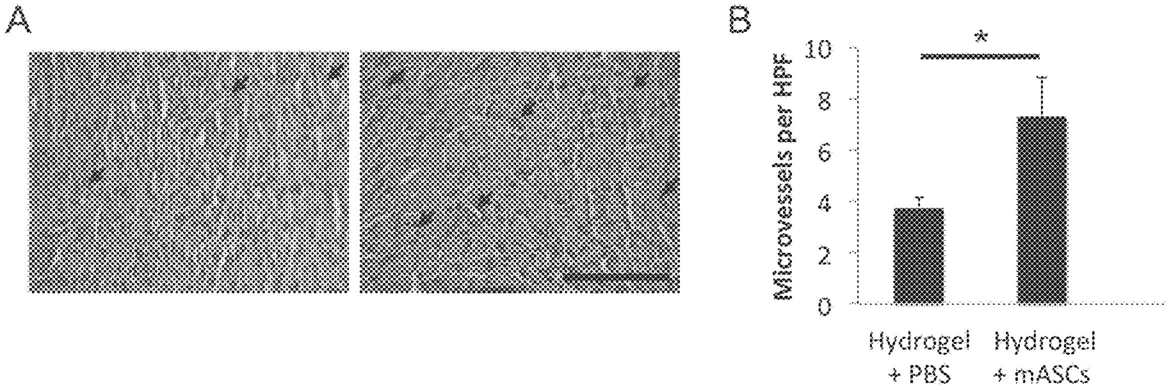
FIG. 7. Murine ASC-Seeded Hydrogels Improve Functional Cutaneous Wound Vascular Density. (A) H&E staining confirmed a significant increase in functional microvessels among the mASC-seeded hydrogel group. DAPI=nuclear stain. Scale bar 100 μm. Arrows indicate microvessels. (B) Quantification of H&E microvessel density. *$p<0.05$; All data are means±one SEM.

Additionally, wounds treated with mASC-seeded hydrogels were significantly more vascular than controls (FIG. 6B,C, FIG. 7). CD31 staining of tissue sections confirmed these results with evidence of increased vascularity among mASC-seeded hydrogel wounds, as compared to unseeded hydrogel controls at day 14 (20010.37 pixels±3839.92 vs. 6113.68±1258.67, $p=0.003$). Additionally, H&E stained tissue sections of day 14 wounds showed a significant increase in microvessel density among the mASC-seeded hydrogel treatment group compared to unseeded hydrogel samples (7.29±1.48 vs. 3.70±0.42, $p=0.01$).

To better understand any ASC cytokine contributions to the wound environment, ELISA assays were performed on day 5 mASC-treated and control wounds. Significantly higher levels of pro-angiogenic VEGF and HGF cytokine expression was detected in mASC-seeded hydrogel treated wounds (113.98 pg/mL±3.47 vs 68.23 pg/mL±8.95, $p=0.03$ and 589.08±102.33 vs 299.53±30.49, $p<0.01$, respectively) (FIG. 6D). These data suggested that the pro-angiogenic profile of ASC-seeded hydrogels was maintained in vivo, and translated to significantly augmented vascularization through multiple paracrine signaling pathways.

Human ASC-Seeded Hydrogels Augment Wound Closure and Vascularization in Nude Mice Given the promising effects of murine ASCs on wound healing, fresh, unexpanded human ASCs (hASCs) were isolated via FACS from healthy, adult-derived lipoaspirates and analyzed for the presence of a similar beneficial influence. Immunocompromised mice were subjected to the splinted excisional wound model and were treated with either hASC-seeded hydrogels or PBS-soaked controls (FIG. 6E,F). Wound area was significantly smaller in the hASC hydrogel treated group compared to control wounds at days 7, 9 and 11 post injury (day 7: 31.09 mm2±4.46 vs. 51.94±7.76, p=0.04; day 9: 15.34±2.81 vs 28.22 mm2±3.90, p=0.02; day 11: 2.04 mm2±1.43 vs 15.64 mm2±3.78), and hASC hydrogel treated wounds closed on average 2.3 days earlier than controls (p<0.01).

Similar to the beneficial effects of hydrogel delivery of murine ASCs, wounds treated with hASC-seeded hydrogels were significantly more vascular than controls based on CD31 staining (17230.75 pixels±2681.98 vs. 7494.82 pixels±1239.38, p=0.001) (FIG. 6G,H). These human data indicated a similar efficacy across cell sources, and supports the use of fresh hASCs within the hydrogel, obviating the need for time consuming ex vivo expansion prior to application.

DISCUSSION

Innovative treatment options are needed to address the significant morbidity and costs associated with chronic and complex acute wounds. In the present study, we have presented a method of almost instantly seeding ASCs into a lyophilized 5% collagen-pullulan hydrogel via capillary force, and demonstrated the efficacy of this cell-based therapy for wound healing applications.

Prior research on scaffold seeding methodologies has focused on increasing seeding efficacy, as a densely seeded construct is crucial for proper tissue formation. Nonetheless, increasingly complex approaches can promote a high seeding density at the expense of time, with protocols often lasting up to several hours or even requiring overnight incubation. To maximize both seeding time and efficiency, a rapid capillary force approach was developed (combining hydrophobic, entropic and capillary forces to promote active, 'bottom-up' cell engraftment) and compared with three previously described seeding methodologies—'top-down' seeding on an orbital shaker, seeding through centrifugation, and direct-injection seeding. Of these techniques, we observed a consistently high seeding efficacy only for orbital shaker seeding and our capillary protocol, with capillary seeding having the additional advantage of being significantly faster than orbital shaking (on the order of minutes as opposed to hours). In fact, capillary seeding was the only seeding methodology that allowed for efficient, rapid cell engraftment, with preservation of cell viability and scaffold micro-architecture, making it highly translatable to the clinical setting.

Utilizing this seeding approach for all subsequent analyses, we further demonstrated the biocompatibility of ASCs within the hydrogel scaffold, with seeded cells demonstrating a sustained viability and migratory capacity in vitro. Moreover, while ASCs cultured under standard conditions demonstrated a steady increase in metabolic activity associated with cellular proliferation, ASCs seeded within hydrogel scaffolds showed minimal proliferation and maintained baseline levels of metabolic activity over seven days. Given that there was no significant cytotoxicity observed with hydrogel culture conditions, these data suggest that the hydrogel induces ASC quiescence and thus may act as a functional niche for this stem cell population. This is consistent with prior studies demonstrating a preservation of cells in the undifferentiated state when embedded in a hyaluronic acid hydrogel, with concomitant maintenance of full differentiation capacity.

Although ASCs are easily accessible and implantable in a hydrogel, the retention of cell stemness remains a key variable. Similar to embryonic stem cells, human bone marrow derived adult mesenchymal stem cells have been shown to regulate plasticity through the expression of embryonic transcription factors, such as the master transcriptional regulator Oct4. Oct4, which is expressed in developing cells of the early blastomere and associated with cell self renewal and pluripotency, has also been shown to be expressed in both murine and human ASCs, but decreases with multiple passages presumably due to the disruption of the stem cell niche. Engraftment of ASCs in the hydrogel, however, resulted in increased transcriptional and protein levels of Oct4, further suggesting that the hydrogel bioscaffold provides a niche-like environment for ASCs and promotes delivery of cells with enhanced stemness characteristics to the wound. ASC upregulation of the pluripotency marker ALP and the mesenchymal stem cell marker CD44 following hydrogel seeding supports this conclusion.

The therapeutic potential of ASC-seeded hydrogels was also demonstrated by transcriptional analyses of plated versus hydrogel-seeded ASCs. Both plated and hydrogel-seeded ASCs expressed numerous growth factors and pro-angiogenic cytokines, substantiating previous findings of the wide spectrum of ASC growth factor/cytokine expression. Nonetheless, we found that ASC engraftment in the hydrogel significantly augmented expression of multiple factors in vitro, including Sdf-1, Mcp-1, Fgf-2, Igf-1, Vegf-a, Eng, Hgf, and Angpt1. These factors play a role in the early inflammatory phase of wound healing, recruit progenitor cells, and facilitate angiogenic processes critical to wound repair and regeneration. Providing insight into the mechanistic underpinnings of hydrogel associated changes in ASC gene expression, prior investigations comparing multicellular aggregates of ASCs to plated ASCs have demonstrated a similar upregulation of growth factors, with concomitant increases in wound healing potential. While this suggests that the three dimensional environment of a cell aggregate and hydrogel scaffold are both capable of augmenting the pro-angiogenic and regenerative potential ASC-based therapies through recapitulation of the stem cell niche, the major translational advantage of the hydrogel to clinical applications is its ability to be seeded with freshly obtained cells without the need for ex vivo expansion.

Prolongation of ASC survival following application is another potential approach to maximize regenerative impact. Our laboratory has previously demonstrated that hydrogel seeding of BM-MSCs enhances their survival in the harsh wound environment as compared to standard cell injection. We observed a similar increase in in vivo ASC survival following hydrogel seeding herein, with this combined data supporting a dual role of the hydrogel for delivery of cells to the wound environment: enhancement of pro-regenerative signaling and prolongation of survival.

Extrapolating this methodology to the clinical setting, the relative ease of lipoaspirate-based ASC collection and immediate hydrogel cell seeding makes our technique ideal for the rapid application of autologous cells to wounds. This approach could theoretically be accomplished in one procedure, and would circumvent the immunoreactive potential of allogenic cell sources. To demonstrate the in vivo regenerative potential of ASC-seeded hydrogels, murine and human cells were separately applied to a splinted murine excisional wound model, which 'humanizes' murine wounds by forcing them to close by re-epithelialization and granulation tissue formation rather than skin contraction. Expanding upon the previously described beneficial effect of ASCs in non-splinted wound models, hydrogels seeded with both culture-expanded murine ASCs and freshly isolated human ASCs were found to significantly improve wound healing at multiple time points compared to unseeded hydrogels, as well as accelerate time to closure and increase wound vascularity. Additionally, the effect on wound closure rates was more pronounced than that reported with shorter-term ASC delivery to similarly splinted wounds using a different bioscaffold, highlighting the influence of both matrix composition and cell delivery time on therapeutic efficacy.

Given the enhanced vasculogenic profile of hydrogel-seeded ASCs, as well as the known paracrine effects of mesenchymal stem cells, the beneficial effects of ASC-seeded hydrogels on vascularization and wound healing observed herein were almost certainly the result of increased ASC-derived growth factors and cytokines within the wound. Nonetheless, the long-term fate of the applied ASCs within cutaneous wound is controversial, as the differentiation of locally administered ASCs into epithelial and endothelial cells within cutaneous wounds has been reported by several groups. Investigating the fate of hydrogel-delivered ASCs within healing wounds, we observed cells predominately in the vicinity of blood vessels, although co-localization to the endothelium was not seen. Quantification of ASC-treated and control wounds also revealed significantly greater expression of multiple hydrogel inducible and vasculogenesis related cytokines within the wound environment. These data support a paracrine mechanism of action for ASC support of neovascularization rather than direct differentiation, regardless of delivery technique.

Collectively, these findings demonstrate not only the regenerative potential of human ASC-seeded hydrogels following wounding, but also the clinically appealing procedural ability to go from cell collection to application in a span of hours. Although the efficacy of ASC-seeded hydrogels remains to be determined in the setting of pathological healing, such as diabetes and ageing, the promising results of this study suggest this therapeutic combination would be similarly efficacious in settings where angiogenesis is impaired.

Figure 8:
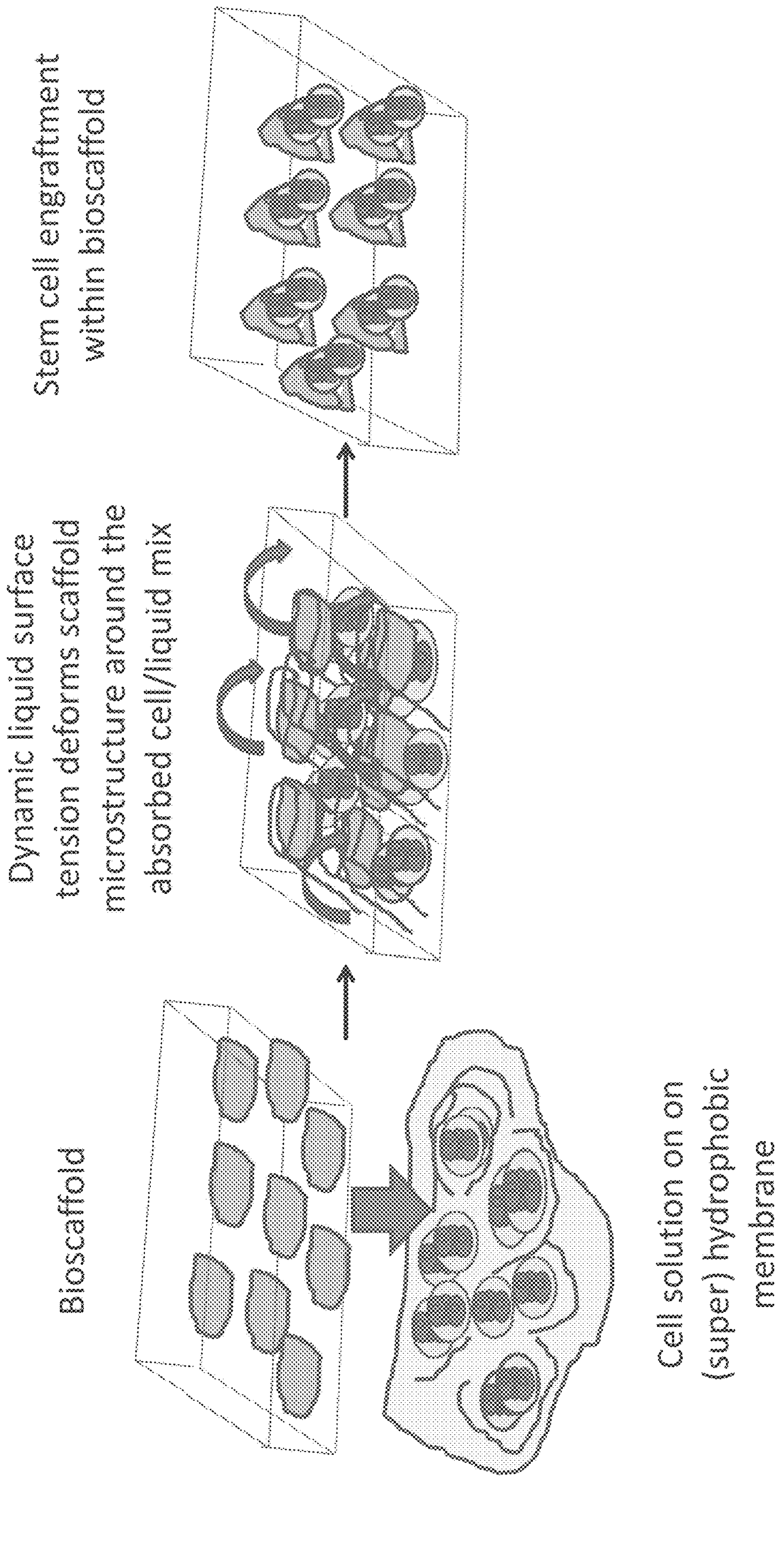
FIG. 8. 'Capillary origami': liquid surface tension deformation of scaffold microstructure around capillary seeded cells.
Figure 9:
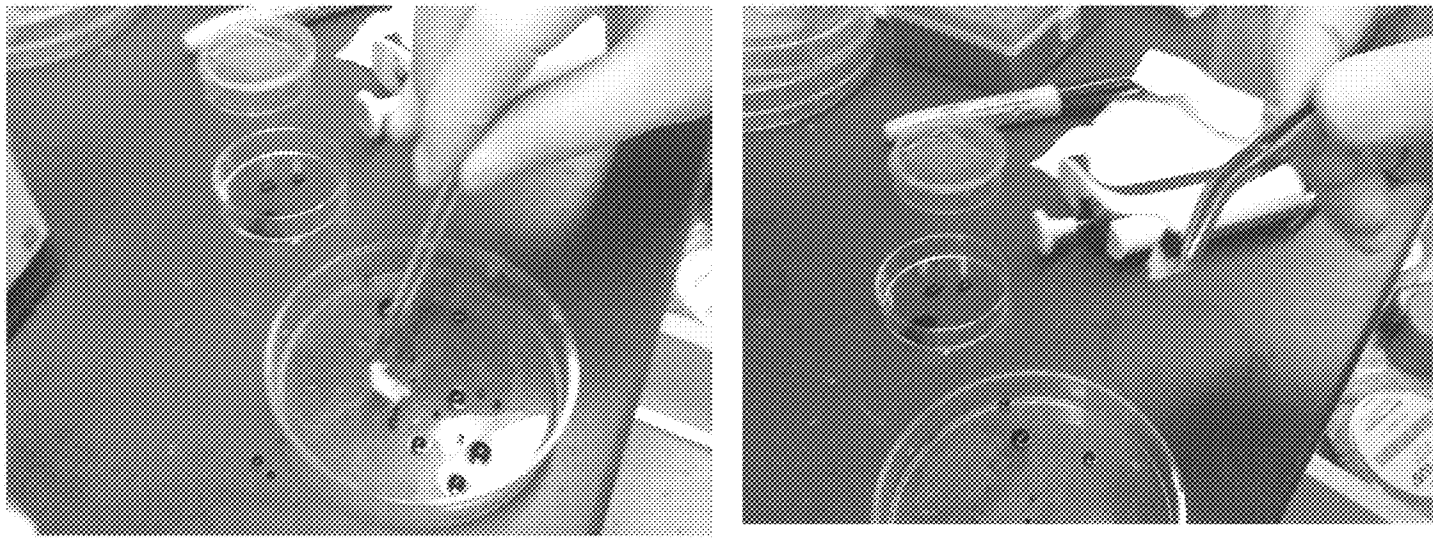
FIG. 9. Superhydrophobic liquid membrane driven capillary seeding.
Figure 10:
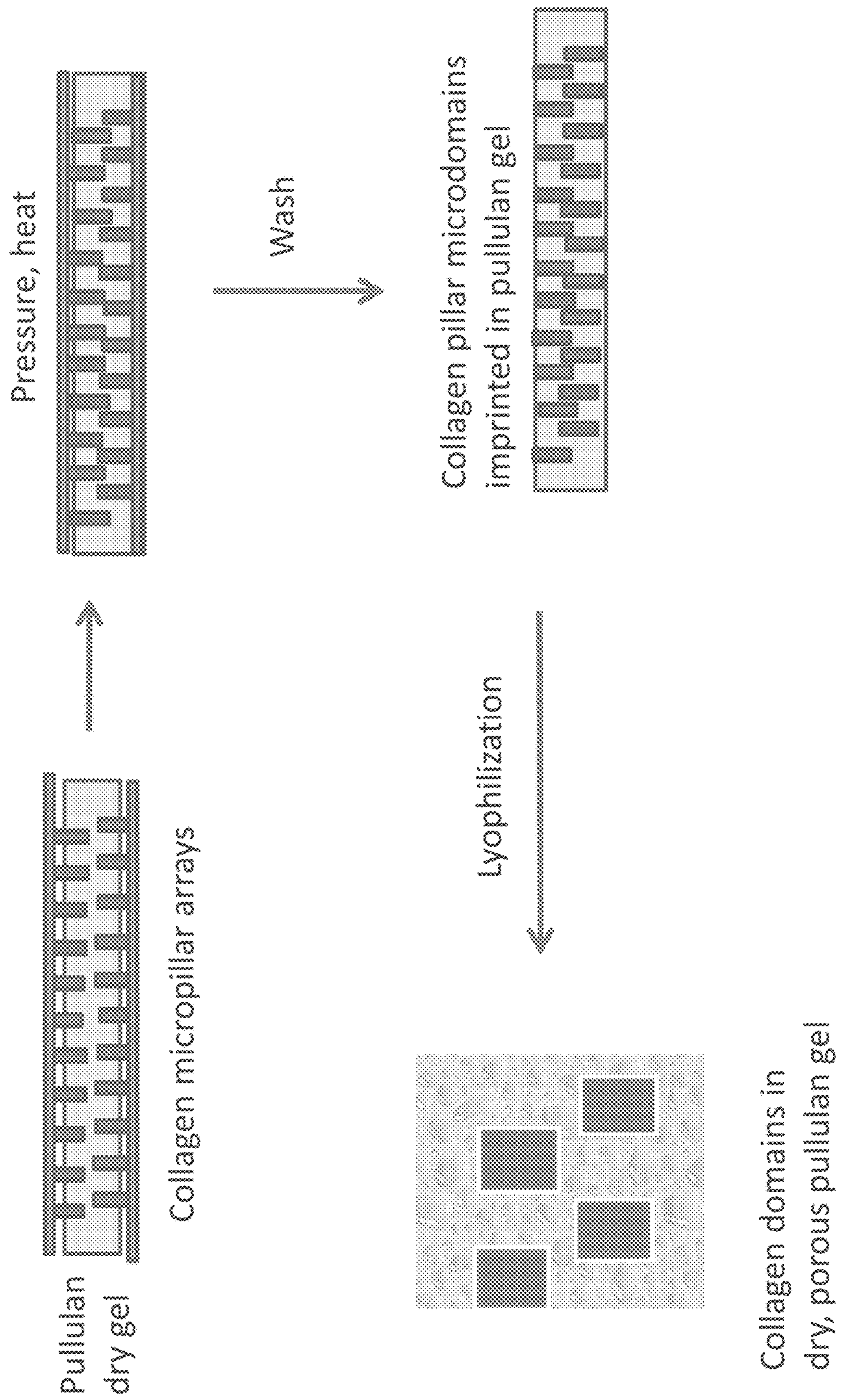
FIG. 10. Creation of encapsulation domains by imprinting collagen arrays within a dry carbohydrate gel (pullulan).

FIGS. 8-10 illustrate superhydrophobic solid and liquid membrane driven capillary stem cell seeding.

CONCLUSIONS

Our biocompatible 5% collagen-pullulan hydrogel can be rapidly seeded with ASCs via capillary force, and provides a functional niche that promotes ASC stemness and growth factor/angiogenic cytokine expression. When applied to excisional wounds, both murine and human ASC-seeded hydrogels promote faster wound healing and enhance angiogenesis and regenerative cytokine expression. ASC-seeded hydrogels are highly translatable due to the ease of cell harvest and potential for immediate application.

What is claimed is:

1. A method of seeding stem, progenitor and/or tissue specific cells within a dressing, comprising:

providing a hydrophobic substance positioned within a tray;

providing an aqueous solution containing a cell population comprised of stem, progenitor and/or tissue specific cells which are maintained or suspended within and retained upon the hydrophobic substance positioned within the tray;

placing a porous hydrogel comprised of a lyophilized collagen in pullulan hydrogel and having a mosaic distribution of a solid film or membrane matrix into contact with the aqueous solution such that at least a portion of the cell population is drawn via a capillary force into micropores of the porous hydrogel and each solid film or membrane matrix deforms around the aqueous solution and the portion of the cell population via the capillary force, wherein the porous hydrogel is sized for placement within or upon a wound; and maintaining contact of the porous hydrogel with the aqueous solution such that the aqueous solution and the portion of the cell population are enclosed within the deformed solid film or membrane matrix via dynamic liquid surface tension such that the aqueous solution and the portion of the cell population are retained within the porous hydrogel.

2. The method of claim 1 wherein the hydrophobic substance comprises a hydrophobic wax material, a super hydrophobic material, a hydrophobic liquid, or a perfluorocarbon liquid.

3. The method of claim 1 wherein the solid film or membrane matrix comprises a collagen, silk, polymer microdomain, or biodegradable microfilm.

4. The method of claim 1 wherein the pullulan hydrogel comprises 5% lyophilized collagen.

5. The method of claim 1 wherein the aqueous solution comprises an aqueous nutrient medium that is placed upon the hydrophobic substance.

6. The method of claim 1 wherein the cell population comprises adipose-derived mesenchymal stem cells or bone marrow-derived mesenchymal stem cells.

7. A method of seeding stem, progenitor and/or tissue specific cells within a dressing, comprising:

placing an aqueous cell mixture solution having a cell population maintained or suspended within an aqueous solution on or in a hydrophobic substance, wherein the cell population comprises stem, progenitor and/or tissue specific cells;

providing a bioscaffold comprising a lyophilized collagen in pullulan hydrogel which has a mosaic distribution of a solid film or membrane matrix, wherein the bioscaffold is placed upon the hydrophobic substance and the aqueous cell mixture solution is absorbed via a capillary force into the bioscaffold such that each solid film or membrane matrix deforms around the aqueous cell mixture solution via the capillary force, resulting in cell engraftment within the bioscaffold; and wherein the aqueous cell mixture solution is enclosed within the solid film or membrane matrix via dynamic liquid surface tension such that the aqueous cell mixture solution is retained within the bioscaffold.

8. The method of claim 7 wherein the hydrophobic substance comprises a hydrophobic wax material, a super hydrophobic material, a hydrophobic liquid, or a perfluorocarbon liquid.

9. The method of claim 7 wherein the solid film or membrane matrix comprises a collagen, silk, polymer microdomain, or biodegradable microfilm.

10. The method of claim 7 wherein the pullulan hydrogel comprises 5% lyophilized collagen.

11. The method of claim 7 wherein the mosaic distribution of the solid film or membrane matrix is imprinted upon the pullulan hydrogel.

12. The method of claim 7 wherein the aqueous cell mixture solution comprises an aqueous nutrient medium that is placed upon top of the hydrophobic substance.

13. The method of claim 7 wherein the cell population comprises adipose-derived mesenchymal stem cells or bone marrow-derived mesenchymal stem cells.

14. The method of claim 7 wherein the pullulan hydrogel comprises a hydrated and washed lyophilized collagen pullulan hydrogel.

* * * * *